United States Patent
Knott et al.

(10) Patent No.: US 9,775,923 B2
(45) Date of Patent: Oct. 3, 2017

(54) DEVICE FOR EXTERNAL STERILISATION OF PLASTIC PARISONS

(71) Applicant: KRONES AG, Neutraubling (DE)

(72) Inventors: Josef Knott, Walkenstetten/Schierling (DE); Hans Scheuren, Regensburg (DE); Ludwig-Lorenz Schillinger, Attenhofen (DE)

(73) Assignee: KRONES AG (DE)

( * ) Notice: Subject to any disclaimer, the term of this patent is extended or adjusted under 35 U.S.C. 154(b) by 350 days.

(21) Appl. No.: 14/061,568

(22) Filed: Oct. 23, 2013

(65) Prior Publication Data

US 2014/0112826 A1   Apr. 24, 2014

(30) Foreign Application Priority Data

Oct. 23, 2012   (DE) .................. 10 2012 110 108

(51) Int. Cl.
  *A61L 2/08* (2006.01)
  *B65B 55/08* (2006.01)
  *B65B 55/10* (2006.01)

(52) U.S. Cl.
  CPC .......... *A61L 2/087* (2013.01); *A61L 2202/23* (2013.01); *B65B 55/08* (2013.01); *B65B 55/10* (2013.01)

(58) Field of Classification Search
  CPC ...................................................... A61L 2/087
  See application file for complete search history.

(56) References Cited

U.S. PATENT DOCUMENTS 3,771,284 A * 11/1973 Boeckmann .......... B67B 3/2073
  53/282
4,594,123 A *  6/1986 Eder ........................ B65C 3/16
  156/456

(Continued)

FOREIGN PATENT DOCUMENTS

CN     101310773       11/2008
DE     102010012569    9/2011  ............... A61L 2/08

(Continued)

OTHER PUBLICATIONS

German Search Report (no translation) issued in corresponding application No. 10 2012 110 108.6, dated Sep. 6, 2013 (5 pgs).

(Continued)

*Primary Examiner* — Donald Spamer
(74) *Attorney, Agent, or Firm* — Hayes Soloway P.C.

(57) ABSTRACT

A device for sterilizing plastic containers includes a transport device for transporting the containers during the sterilization along a predefined transport path, a clean room within which the containers can be transported during sterilization, wherein the clean room is delimited by at least one wall with respect to the environment, and a first external application device for sterilizing at least a section of the outer wall of the containers. The first external application device has a source of charge carriers for generation of charge carriers, and includes a first moving device which moves the containers at least intermittently in the longitudinal direction during their sterilization. The device also includes a rotary device which rotates the containers about their longitudinal direction at least intermittently during the sterilization, wherein the rotary device and the moving device are preferably configured in such a way that a rotation of the containers is enabled during a movement of the containers in their longitudinal direction.

23 Claims, 7 Drawing Sheets

(56) References Cited

U.S. PATENT DOCUMENTS

| | | | | |
|---|---|---|---|---|
| 4,642,071 | A * | 2/1987 | Botton | F16H 7/18 474/63 |
| 5,396,074 | A * | 3/1995 | Peck | G21K 5/10 250/453.11 |
| 8,294,126 | B2 | 10/2012 | Humele et al. | 250/492.3 |
| 8,729,499 | B2 | 5/2014 | Knott et al. | 250/455.11 |
| 2005/0098740 | A1 * | 5/2005 | Bol | A61L 2/087 250/492.1 |
| 2005/0188651 | A1 * | 9/2005 | Clusserath | B67C 7/0073 53/136.1 |
| 2010/0123090 | A1 | 5/2010 | Nishino et al. | 250/491.1 |
| 2010/0209290 | A1 | 8/2010 | Cirri et al. | 422/22 |
| 2011/0012030 | A1 * | 1/2011 | Bufano | A61L 2/087 250/492.3 |
| 2011/0133369 | A1 | 6/2011 | Martini et al. | 264/523 |
| 2011/0259709 | A1 * | 10/2011 | Grossmann | B65G 33/04 198/339.1 |

FOREIGN PATENT DOCUMENTS

| | | | |
|---|---|---|---|
| EP | 1982921 | 10/2008 | A61L 2/08 |
| EP | 2149500 | 2/2010 | B65B 55/08 |
| EP | 2213578 | 8/2010 | B65B 55/08 |
| EP | 2319678 | 5/2011 | A61L 2/20 |
| EP | 2371397 | 10/2011 | A61L 2/08 |
| EP | 2594493 | 5/2013 | A61L 2/08 |
| EP | 2594495 | 5/2013 | A61L 2/08 |
| WO | WO2009052800 | 4/2009 | B29C 49/46 |

OTHER PUBLICATIONS

Extended European Search Report (no translation) issued in related application No. 13189412.3, dated Jan. 23, 2014 (7 pgs).

Chinese First Office Action, Appln. No. 201310503505.5, dated Apr. 3, 2015 (2 pgs).

* cited by examiner

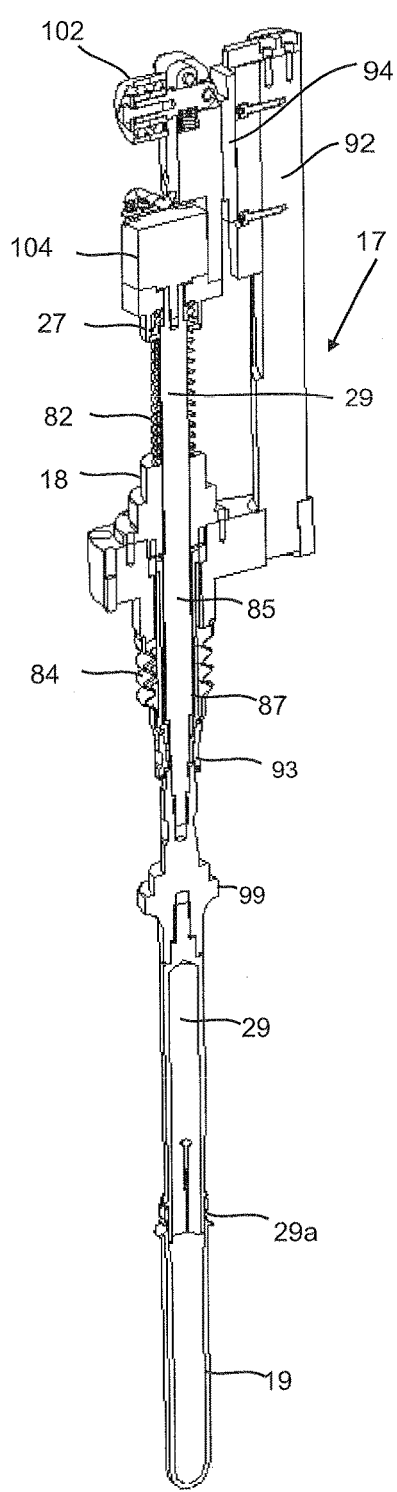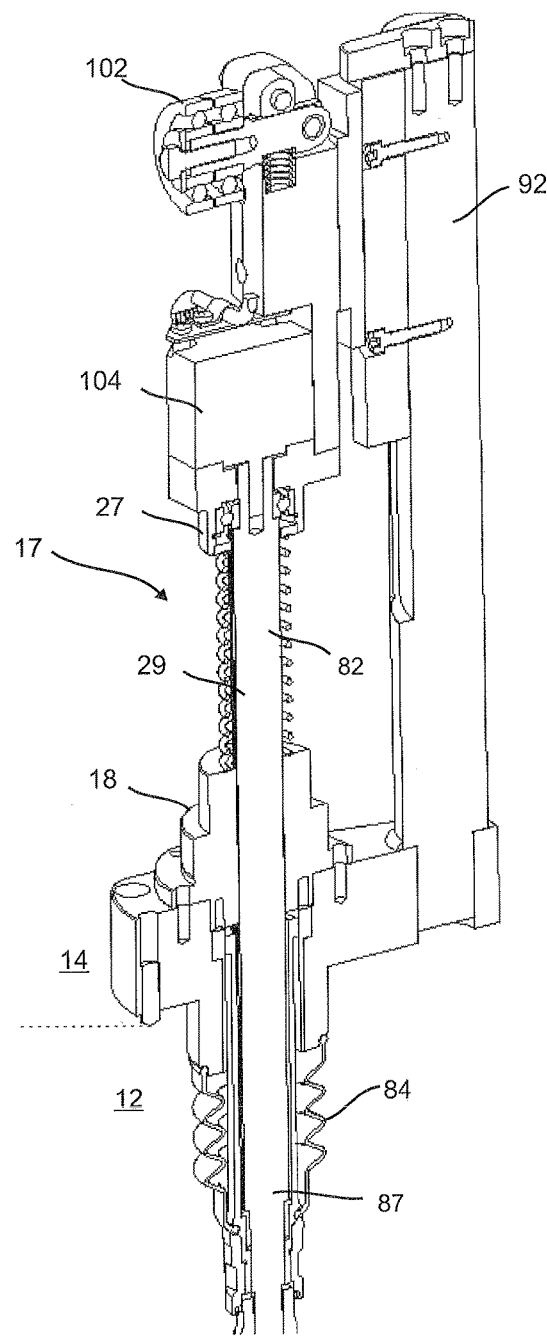
Fig. 5
Fig. 6

DEVICE FOR EXTERNAL STERILISATION OF PLASTIC PARISONS

BACKGROUND OF THE INVENTION

The present invention relates to a device and a method for sterilising plastic containers and in particular plastic parisons. It is known from the prior art that in the context of the production of beverage containers the containers to be filled are also sterilised to some extent. For this purpose in the prior art sterilisation methods are usually used which employ chemical agents, such as for instance hydrogen peroxide or peracetic acid. Recently, however, attempts have been made to dispense with the use of such chemicals. Accordingly devices and methods are also known from the prior art in which the sterilisation takes place by the use of radiation sources, such as for example ultraviolet light or also electron radiation sources. The present invention is therefore described in particular with reference to sterilising devices which apply charge carriers to the containers in order to sterilise the containers.

The current devices which are available on the market and are used for sterilisation usually have an electron generating device and also a beam finger which serves for disinfection of the internal surfaces of the containers. In addition such system also has electron generating devices which also treat the internal surfaces from the exterior through the container. In the treatment from the exterior the electrons must generally be accelerated considerably more, since the wall of the container to be treated must be penetrated and in spite of the weakening the electrons must always still contain sufficient energy in order to act to sterilise the inner surface. The X-ray radiation produced in this case must be screened off from the environment by suitable screens. In addition the entire container material is loaded with a radiation dose.

Arrangements which operate with a beam finger generally use substantially lower acceleration voltages and thus fewer shields and lower radiation doses in the container material. However, in order also to sterilise the containers externally a further process step is necessary. The external treatment can be carried out before, during or also after the internal treatment.

The object of the present invention therefore is to provide a device and a method which enable an improved external sterilisation of the containers and preferably also an improved overall sterilisation thereof.

SUMMARY OF THE INVENTION

A device according to the invention for sterilising plastic containers has a transport device by means of which the containers can be transported during sterilisation along a predefined transport path. Furthermore, the device has a clean room within which the containers can be transported during sterilisation, wherein this clean room which is separated by means of at least one wall from the environment.

In addition the device has a first external application device for sterilising at least one portion of the outer wall of the containers, wherein this external application device has a source of charge carriers for generating charge carriers, and also a first moving device which at least intermittently during sterilisation moves the containers with respect to the external application device in the longitudinal direction of the containers.

According to the invention the device has a rotary device which rotates the containers at least intermittently during sterilisation about their longitudinal direction, wherein the rotary device and the moving device are preferably designed in such a way that a rotation of the containers is possible during a movement of the containers in their longitudinal direction possible or that these rotations are made possible chronologically one after the other.

It is therefore proposed that the plastic containers are moved in their longitudinal direction and are also rotated about their own longitudinal axis during this movement. In particular the containers can be rotated about their own axis during entry or before or after entry and/or during or before or after exit from a sterilisation zone. Holding devices are advantageously provided for holding the containers and particularly preferably these holding devices grip or hold take effect or hold the containers so that furthermore an unhindered irradiation of the plastic containers is possible.

In a further advantageous embodiment the transport device has a rotatable carrier. A plurality of holding devices for holding the plastic containers is advantageously disposed on this rotatable carrier.

In a further advantageous embodiment the device has a mechanical coupling device which couples together the movement of the containers in their longitudinal direction and the rotary movement of the containers about their longitudinal direction.

Advantageously this coupling device has at least one coupling element which is or can be driven by a driving device and which particularly preferably drives a further coupling element. Thus for example as coupling element two interengaging tooth systems, for instance of toothed belts or toothed wheels, could be provided as coupling elements. One of these two tooth systems could be driven by a drive unit, such as for instance an electric motor.

In a further advantageous embodiment a further sterilising device is also provided which sterilises the plastic containers from the interior. In this case this further sterilising device preferably has a rod-like body which is introduced into the interior of the plastic containers. The plastic containers are advantageously so-called plastic parisons, which are transformed into plastic containers in particular by a stretch blow-moulding process.

The sterilisation process for the external surface and the sterilisation process for the internal surface are advantageously separated from one another in terms of time and/or location. This means that a sterilising device for sterilising the internal surface is disposed along the transport path of the plastic parisons before or after the sterilising device for the external surfaces. The advantage of this separation of the external disinfection from the process of internal disinfection is that a treatment of all the container surfaces is made possible without any shading effect by container transport elements. Therefore the container transport elements which transport the containers in the region of the external disinfection are equipped with gripping systems which grip the containers from the interior.

The containers are preferably held at least intermittently with an internal gripper and are preferably also at least intermittently with an external gripper. While electrons are applied to the plastic parisons it should be ensured that the gripping elements do not create any shading effects, that is to say they do not cover surfaces of the plastic parison which therefore are not sterilised by means of electrons. Thus for example during the external sterilisation an internal gripper could be used which does not cover or shade any external surfaces of the containers.

A device according to the invention preferably has at least one feed starwheel, a subsequent external sterilisation unit, a transport starwheel which is designed in particular as a pitch reduction starwheel in order to transport the plastic containers further starting from the external disinfection device, an internal disinfection device and a discharge starwheel. In this case the said devices are preferably disposed in the order given here, that is to say in particular in the sequence: external disinfection device (or external sterilisation device)—pitch reduction starwheel—internal disinfection device (or internal sterilisation device). However, other sequences would also be conceivable, for instance firstly an internal disinfection device and then an external disinfection device. In addition it would also be possible to provide, for the external disinfection or external sterilisation, two or more modules or devices which can be disposed for example on both sides with respect to the transport path of the plastic parisons.

During the transport on the feed starwheel the plastic parisons are preferably held from the exterior, for example below the support ring. Then the plastic parisons are preferably transferred to internal grippers and thus are held at the mouth or via their inner wall. Thus during the transport through the external sterilisation electrons can be applied to the entire external surface of the plastic parisons. As they are transferred to the aseptic pitch reduction starwheel the plastic parisons are preferably transferred from the internal gripper to a further external gripper and transported further to the internal treatment, where the plastic parisons are held by means of external grippers.

Accordingly a complete internal disinfection can take place here without restriction. The discharge starwheel preferably also has external grippers, in particular so-called double clips, so that the plastic parisons from the internal disinfection (during which the plastic parisons are preferably held with a single clip) can be optimally and reliably transferred to the discharge (here the plastic parisons are preferably held by means of double clips).

Thus on the entire path through the module the plastic parisons are gripped so that no impairment of the sterilisation of the surfaces by e.g. clip elements can occur.

For the sterilisation of the internal surfaces gripping systems are advantageously provided which grip the containers from the exterior, for example in the region of their mouth or below their support ring. Therefore the external sterilisation of the containers preferably takes place before or after the internal sterilisation. Particularly preferably the external sterilisation takes place first and then the internal sterilisation.

The gripping systems which are used in this case, that is to say in particular the internal grippers and/or external grippers, are advantageously constructed according to hygienic standpoints and particularly preferably can also be easily sterilised. In an advantageous embodiment the internal gripper is a collet chuck which can preferably be reliably transported without further clamping devices.

In a further advantageous embodiment the gripping system used is designed for gripping the containers in such a way that it can grip the containers internally at the transfer points. Therefore the gripping system is preferably able to carry out a stroke in the direction of the container axis or the above-mentioned longitudinal direction. This stroke can advantageously be carried out by means of a curve segment of a circumferential curve, a pneumatic actuation, a servo-driven linear guide or with other conceivable designs.

Also, as mentioned above, the rotary drive described above can be designed in such a way that in each case servomotors are provided. However, in addition a central cam gear or a toothed belt can be used. It is also conceivable to drive the cam gear or the toothed belt in order when the gear meshes on the outer gear rim to obtain a possibility for influencing the rotation (such as a setting the uniform dosage distribution on the periphery of the container).

In a further advantageous embodiment the coupling device has a toothed belt, and in particular a flexible toothed belt. This toothed belt can extend along a circumferential line. In a further advantageous embodiment the coupling device has at least one coupling element which can be moved in two opposing directions of movement (for example in two different directions of rotation or directions of circulation). If a toothed belt is provided as coupling element, this can have an external toothing or also an internal toothing.

If the coupling element is designed for example as a gear the gear can be rotated in the circumferential direction on both sides. If the coupling element is designed as a toothed belt it is possible for the toothed belt to be moved or driven in both directions. In this case it is also possible that the respective driven coupling element is driven at different speeds.

Due to this rotation of the containers during the external disinfection a uniform dose can be applied to the external surface of the plastic containers. In addition in this way it is also possible to economise on sterilising devices. It would be basically possible to fit sterilising devices on both sides of the transport path of the containers. However, due to the rotation provided here it is also possible, if need be, to use only one sterilising device. In this way on the one hand it is possible to save on production costs and on the other hand the TCO (Total Costs of Ownership–total operating costs) can also be improved.

Therefore in a further advantageous embodiment at least one element of the rotary device is disposed outside the clean room. In a further advantageous embodiment at least one element of the moving device is also disposed outside the clean room. This means that any drive means, such as motors or also guide curves, are preferably disposed outside the clean room and in each case the motion is transferred into the interior of the clean room. Advantageously therefore in particular only the gripping system with the actual holder for the containers is accommodated in the clean room and the controls are preferably disposed completely outside the clean room. This means that the gripping system or the total moving device can be disposed through a clean room boundary.

In a further advantageous embodiment the device has at least one sealing device which seals the movement of the containers in the longitudinal direction thereof and/or the rotation of the containers about the longitudinal direction thereof. More precisely this sealing device effects sealing of the clean room in this region into which the movements are introduced. Therefore the gripping device for gripping the containers is advantageously separated by an axial and a radial seal from the outer room or an unsterile environment.

In order to obtain a hygienic or aseptic sealing of the lifting/rotating mechanism it is proposed here that a sealing device—for instance in the form of an elastomer bellows—takes care of the axial sealing. The radial sealing is advantageously provided by a radial sealing element.

It is pointed out that the seal described here is also applicable independently of the above invention, that is to say in particular without the simultaneous movements described above. The applicant reserves the right to seek its own patent protection for this.

Since the elastomer bellows does not transmit any transverse forces or torques it is preferably provided with an additional torque support which can absorb the transverse forces generated by the rotation of the gripping system. Such a torque support is preferably movably mounted in its axial position and particularly preferably also bears the radial seal which seals the rotating axis of the gripping system with respect to the clean room.

In addition it would also be conceivable to produce a bellows, for example a gaiter, from Teflon and/or similar materials known in the field of aseptics which due to its inherent rigidity could also optionally be used without additional torque support for the rotational transverse forces. Advantageously such rotational seal could be placed adjacent to an axial seal. However, a torque support for increasing the service life is equally conceivable.

In a further advantageous embodiment the device has at least one reflector element for reflecting charge carriers and in particular electrons, which is disposed in such a way that the containers can be transported between the first external application device and this reflector element. In order to increase the applied dose it is conceivable to place behind the plastic container a type of reflector which is made for example from steel or stainless steel, preferably even from a material with a higher density than steel or at least has a thin layer of this material on a support material.

In a further advantageous embodiment the above-mentioned gripping system is configured as a clamping sleeve. This clamping sleeve can be introduced through a mouth of the plastic containers into this container and therefore holds the container from the interior.

In a further advantageous embodiment this clamping sleeve is configured in such a way that for a resilient action for gripping and securing the container no further components are necessary are and the resilient action alone is based on the implementation and choice of material of the sleeve. In this way for example a resilient material can be used which is introduced into the mouths of the plastic containers.

In a further advantageous embodiment a rate of rotation is varied as a function of the distance of the container to be treated from the radiation device in order preferably to obtain the most homogeneous dose distribution possible.

In a further advantageous embodiment the device has a second external application device which also applies radiation to the outer wall of the containers. In this case this second external application device can be offset with respect to the first external application device along the transport path of the plastic containers. It would also be possible for this second external application device to be disposed on the other side than the first external application device with regard to the transport path of the containers. Thus the containers could be guided between these two external application devices. However, it would also be possible for the second external application device to be both offset in the circumferential direction or along the transport path and also disposed on the opposite side relative to the transport path of the containers (compared with the first external application device).

In a further advantageous embodiment the above-mentioned coupling device has two interengaging gears. These interengaging gears serve for transmission or execution of the rotary motion of the gripping elements on which the plastic containers are disposed and thus also the plastic containers themselves.

In this case one gear can preferably be displaced with respect to the other gear whilst retaining an engagement between the gears. Thus it is possible that one of the two gears is designed as a long wheel. This long wheel is advantageously disposed stationary and a second wheel, which for example directly drives the plastic containers, can be disposed displaceably with respect thereto.

An embodiment of the device for sterilising containers is preferred, in which the containers to be sterilised are parisons, in particular parisons for (i.e. for production of) containers for beverages and/or other fluid media. This makes possible a smaller surface to be sterilised due to the significantly lesser expansion (or size, length and/or diameter) of the parisons by comparison with finished containers. As a result it is also possible to give the application device smaller dimensions. Preferably the amount of radiation, radiation intensity, acceleration voltage and/or other parameters can also be improved, so that the energy requirement of the device and/or the production or purchase costs can be reduced.

An embodiment of the device for sterilising from containers is preferred in which the transport path is curved at least in one section in which the first external application device is disposed for sterilising at least one section of an outer wall of containers. Due to this embodiment it is possible to use transport equipment, such as for example transport starwheels, in which the transport path is of substantially meandering design at least in sections. This embodiment also enables a particularly compact construction.

It is preferably provided that in the device for sterilising containers a further external application device is disposed on the side of the transport path opposite the first external application device, wherein the external application device and the further external application device are particularly preferably disposed offset along the transport path.

This embodiment with two external application devices which are opposed with respect to the transport path is advantageous since without a rotation of the containers about their own longitudinal axis the application of the charge carriers to the containers is possible from both sides. The transport device can therefore be significantly simplified and for example a mechanism for complete rotation of the containers and their longitudinal axis are omitted. If in spite of the opposing external application devices the sterilisation in the edge regions is nevertheless insufficient, a pivoting movement of the containers is conceivable. In this case a pivoting movement should be understood as essentially a rotation of the containers by fractions of a complete revolution. The control necessary for this is substantially simpler than that for complete rotations and nevertheless ensures sufficient sterilisation of all external surface regions of the container.

In order to prevent charge carriers from being accelerated directly against one another, which could lead inter alia to particularly high charge carrier density in the overlap zone of the emitted charge carrier clouds or to damage to the external application device due to the constant application of charge carriers which are emitted by the opposing external application devices in the direction the direction thereof, the external application devices are preferably offset along the transport path by an angle between 2 and 20°, particularly preferably between 5 and 10°, of a circle of curvature of the transport path.

Thus the maxima of the charge carrier clouds emitted by the external application devices in direction of the transport path are spaced along the transport direction of the containers by preferably at least 2 cm, preferably at least 5 cm, particularly preferably at least 10 cm and preferably at most 200 cm, preferably at most 100 cm, particularly preferably at most 50 cm. As a result, during the transport the containers first of all enter into the sphere of influence of an external application device which applies charge carriers to the containers. At a later time, when the container enters a sphere of influence of the other external application device, located downstream, of the other external application device it has charge carriers applied to it. Thus the spheres of influence the two external application devices can overlap.

At least one external application device is preferably disposed substantially outside a clean room. In this context "substantially outside the clean room" should be understood to mean that a majority the external application device is accessible from the exterior and without opening the clean room—and thus without any possible contamination of the clean room—, but the charge carrier exit window is disposed in a wall of the clean room so that the charge carriers from the external application device can be emitted into the clean room and onto the container to be sterilised.

In a region of the transport path in which the first external application device is disposed, the device for sterilising containers is surrounded at least in sections by a radiation shielding system with at least one outer radiation shielding device and one inner radiation shielding device, by which radiation emitted by the first external application device can be at least partially absorbed.

The embodiment with two radiation shielding devices makes it possible to construct a transport channel which extends between the two radiation shielding devices and in which the containers can be transported. In this connection an inner radiation shielding device is understood to be a radiation shielding device which shields against charge carriers in the direction of an inner face of the device.

Since advantageously there are no persons present in this area this radiation shielding device can, if need be, be of less strong design than an outer radiation shielding device. This preferably also shields the environment in which persons may also be present—at least temporarily—against the charge carriers and/or the radiation. In a preferred embodiment of the arrangement of the external application devices along a section of the circumference of a circle the inner radiation shielding device is disposed in a radially inner position with respect to the transport path and the centre of the circle and the outer radiation shielding device is disposed in a radially outer position with respect to the transport path and the centre of the circle.

Accordingly the outer radiation shielding device is preferably disposed on a radially outer side of a curved transport path. Since the external application devices preferably constitute the strongest charge carrier generating arrangements, a particularly strong shield is necessary in the sphere of influence thereof. Therefore the radiation shielding device disposed in this region has stronger shielding characteristics than a radiation shielding device which is disposed along another region of the transport path.

Due to the curvature of the transport path in the region of the external application devices it is possible that radiation and/or charge carriers are reflected—preferably at least twice, particularly preferably several times—by the external radiation shielding device, and are preferably reflected or deflected in the direction of the containers to be sterilised.

A device for sterilising containers is preferred in which the radiation shielding system has a portion which is stationary during the transport of containers along the transport path and another portion which is movable relative to the first portion during the transport of containers along the transport path.

By this variant it is possible for gripping or holding elements to follow the movement of the relatively movable portion of the radiation shielding system and to move (at least with a vector component) parallel to the transport direction of the containers.

The speed of the movable relative portion of the radiation shielding system can be adapted at least in a section of the transport path to a speed at which the containers are moved along the transport path.

The gripping or holding elements preferably penetrate the relatively movable portion of the radiation shielding system at least in some sections, so that a part of the gripping or holding elements is disposed in the interior of the transport channel arranged is and can grip or hold the containers there. Another part of the gripping or holding device is preferably disposed outside the transport channel. This part disposed outside can for example have components which require intensive maintenance, so that maintenance thereof is possible without having to open the sterile transport channel. Elements of a lifting, rotating, pivoting and/or transport mechanism are preferably located outside the sterile transport channel.

In particular in the treatment of parisons it is necessary to adapt the lifting mechanism to the small dimensions of the parisons by comparison with finished containers.

The containers are preferably held or transport at least in the region of the external sterilisation by a clamping sleeve substantially in one piece.

A device for sterilising from is preferred in which the internal application device for sterilising at least a section of an inner wall of containers has an accelerating means with a lower acceleration voltage than an accelerating means of the first external application device.

The internal application device must be introduced at least partially into the interior of the container. Therefore there are particular requirements for the dimensioning thereof, which make strong shields, large transformers, bulky cooling elements and other large components disadvantageous. In particular in the internal sterilisation of parisons, because of the low expansion thereof there is no need for particularly strongly accelerated charge carriers. Parisons often have an internal diameter of <5 cm, <3 cm or even <2 cm on, so that the charge carriers do not have to travel large distances between a charge carrier exit window located in the interior of the container and the internal surface of the container. Therefore for in this case low acceleration voltages are sufficient the internal application device. A reduction in the acceleration voltage to the necessary level offers advantages in the energy efficiency, the operating costs and the expenses for sufficient shielding of the environment relative to charge carriers and/or radiation.

By contrast the external application device emits charge carriers over a greater area, so that higher acceleration voltages and/or greater charge carriers are required there. Accordingly a stronger shield is advantageous in the vicinity thereof.

In order nevertheless to be able to design the external application device to as much space as possible whilst at the same time being able to apply charge carriers to the entire required surface region of the container, in a preferred embodiment of the device for sterilising containers at least the first external application device, and preferably also a further external application device, has a substantially rectangular or oval charge carrier exit window, wherein preferably at least one longitudinal axis of the charge carrier exit window is inclined relative to a longitudinal axis of the container to which charge carriers are applied. The total external application device is preferably inclined relative to a longitudinal axis of the container to which charge carriers are applied. The charge carrier exit window is preferably substantially rectangular.

The expression "inclined relative to a longitudinal axis of the container to which charge carriers are applied" should be understood to refer to charge carrier exit windows or also external application devices in which a main axis is inclined relative to the longitudinal axis of the container to be acted on by charge carriers. In this connection main axes should be understood to be axes which constitute a preferred direction or maximum expansion in a direction of the exit window or of the external application device housing or axes perpendicular thereto. Examples of this are the large half-axis and the small half-axis of an oval (elliptical) exit window or external application device housing, the perpendicular bisector of a rectangular exit window or external application device housing or the like. Also the main axes of the external application devices are preferably inclined relative to one another.

Due to the inclined arrangement of the external application devices and/or of the charge carrier exit window, the section in which a container is sterilised during the transport along the transport path can be extended. Simultaneously, however, it can also be ensured that the container is exposed to the charge carriers over its entire height or length, but at least over the entire region of the external surface to be sterilised. As set out in detail in the description of FIG. 4, due to the inclination of the charge carrier exit window and/or the external application device a region in the form of a parallelogram is produced in which the surface over which the container travels while being transported and the charge carrier cloud emitted by the external application device overlap.

This region is dimensioned so that the container passes through it with all the outer surfaces to be sterilised. Therefore the parallelogram which delimits this region preferably has a height (above the base line) which corresponds at least to the length or height of the container. Due to the inclination the length of the transport path in which a respective portion of the external container surface is sterilised can preferably be enlargede by a ratio which (disregarding scattering effects of the charge carriers) corresponds approximately to the sine of the angle of inclination to the width of the charge carrier exit window.

Furthermore a device for sterilising containers in which the device has an introduction device by means of which the internal application device can be introduced at least in sections into the interior of a container, wherein the container and the second charge carrier exit device are movable relative to one another, preferably in a longitudinal direction of the container.

In a further preferred embodiment of the device for sterilising containers, contacts a section of a support plate movable with respect to the first portion of the radiation shielding system at least intermittently contacts sealing and/or sterilising medium located in a channel in order to seal a clean room extending at least in sections along of the transport path. The support plate is preferably movable synchronously with a portion of the radiation shielding system which is movable relative to the first portion of the radiation shielding system. The support plate preferably forms a boundary of the clean room.

Accordingly on the side of the relatively movable portion of the radiation shielding system the transport channel is closed off by a hydraulic seal with respect to the environment. This is preferably a ring which turns according to the movement of the containers along the transport path and shields the transport path or the section of the transport path in which the external sterilisation takes place.

As a result it can be ensured that the interior of the transport channel is closed off relative to the environment and no foreign bodies, contaminants, microorganisms, spores and the like can penetrate into the transport channel. The medium is preferably a medium, which has both sealing and sterilising characteristics. More preferably it is a liquid or viscous (low-viscosity) medium, so that in the interior of the transport channel an overpressure can be built up which prevents the inflow of ambient air and entrained impurities into the sterile transport channel. Gases are also possible as medium, wherein they are preferably made to flow and kept flowing in such a way that a penetration of foreign matter into the clean room is prevented. Accordingly in particular a flow is maintained which travels from the direction of the clean room in the direction of the environment.

Below the channel in which the sealing and/or sterilising medium is located a further channel is preferably located, into which medium from the upper channel can be introduced, for example sucked in. The sealing and/or sterilising medium is preferably an aqueous solution of a sterilising active substance (sterilising medium). It is particularly preferably to use as the sealing means a gas stream, preferably an air stream, in particular (filtered) ambient air, which by its flow prevents the penetration of contaminants into the interior of the clean room.

Furthermore a device for sterilising containers in which the section of the support plate movable with respect to the first portion of the radiation shielding system can be separated at least intermittently from the sealing and/or sterilising medium located in the channel in order to enable access to the clean room extending at least in sections along the transport path, in particular for maintenance and/or cleaning. In particular it is provided that the portion of the radiation shielding system which is movable relative to the first portion, in particular an upper part the external sterilisation device, can be removed upwards. This offers the possibility of opening the transport channel, which was previously closed off with respect to the environment, in order to clean it. By way of example an additional disinfecting or sterilising medium can be introduced into the transport channel. Moreover it is possible for any containers located in the transport channel which might have come loose from the holding devices to be removed in order to prevent damage or loss of further containers.

Furthermore an embodiment of the device for sterilising containers is preferred in which the device has a lifting device by means of which the containers can be moved along their longitudinal direction during the transport along the transport path. Such a lifting device is preferably located in the region of a transport device which transports the containers during the external sterilisation thereof. In this way it is possible to orient the containers relative to the external application device in particular during the external sterilisation. In particular, in the case of charge carrier exit windows inclined with respect to the longitudinal axis of the container it is therefor possible to position the containers in each case so that charge carriers can be applied to the intended region of the outer container surface.

This lifting mechanism preferably has a motor and a threaded rod guide which are adapted to the limited space available in the region of the external sterilisation device. However, the said movement of the containers in the longitudinal direction thereof could also be implemented by the use of guide tracks or control curves.

The charge carriers are in particular electrons, but it would also be conceivable for other charge carriers such as ions to be used.

The charge carrier exit window is particularly preferably produced from a material which is selected from a group of materials including titanium, quartz glass, diamond, combinations thereof and the like.

Furthermore the present invention also relates to a plant for handling containers which comprises at least one device of the type described above, wherein this device is preferably disposed downstream relative to a heating means for heating plastic parisons and upstream of a filling device, preferred upstream of a transforming device for containers.

With such a plant it is possible to carry out an internal and external sterilisation of containers in particular with the high cycle rates and throughputs used for the production and filling of containers.

In particular if the described device is disposed downstream with respect to a heating device and upstream with respect to a transforming device a rapid sterilisation and rapid transport through the device is necessary. If the sterilisation process or the transport through the sterilisation device takes too long there is a danger of the cooling of the containers, in this case the parisons. Therefore the device is preferably suitable for transporting the containers along of the transport path and thereby sterilising them within a time window of less than 20 seconds, preferably less than 15 seconds, particularly preferably about 11 seconds.

The plant preferably has a transport arrangement which moves the containers along a predetermined transport path, in particular also during sterilisation of the containers. The transport device is advantageously a rotatable carrier on which a plurality of gripping elements is particularly preferably disposed.

The plant preferably has a device for filling containers and the device according to the invention is disposed upstream relative to this device.

Furthermore it is preferred that the plant has at least one transport element, preferably a transport starwheel, which is suitable for taking up a container from a device for sterilising containers and transferring it to a device for transforming the containers.

Such a plant preferably has in each case a so-called lock star for introduction or removal of the containers into or out of a device of the type described above. These two lock stars are preferably different. In particular because the pitch spacing is modified within the device an identical design of the lock stars is not possible.

Furthermore the present invention relates to a method for sterilising plastic containers, wherein the containers are transported by means of a transport device within a clean room and during this transport external surfaces of the containers are sterilised by irradiation with charge carriers and wherein the containers are moved at least intermittently in their longitudinal direction.

According to the invention the containers are rotated about their longitudinal direction at least intermittently during sterilisation.

In this case it is possible, that at least at times this rotation of the containers and the movement of the containers in their longitudinal direction take place simultaneously. However, it would also be possible that first of all a movement in the longitudinal direction of the containers takes place and then a rotation. It would also be possible for this rotational movement in turn to be followed by a movement in the longitudinal direction of the plastic containers.

Thus it is possible for the radiation devices to be inclined and in this way for the travel of the containers to the external radiation devices to be extended. In particular in this case the rotation and preferably also the movement in the longitudinal direction take place during the sterilisation.

In a preferred method the movement of the containers in their longitudinal direction and/or the rotation of the containers about their longitudinal direction is sealed in order to maintain the clean room.

A variant of the method for sterilising containers is preferred in which the parisons, in particular parisons for containers for beverages and/or other fluid media, are sterilised. This has the advantage, that by comparison with finished moulded containers substantially smaller surfaces are to be sterilised and thus the process can be configured much more efficiently. Moreover the entire device can have smaller dimensions, which results in a significant weight reduction. Furthermore as a result a higher process stability of the charge carrier application devices, that is to say the external application device and the internal application device, is made possible since the energy used and the resulting window loading are less because of the dimensions of a parison.

A variant of the method for sterilising containers is further preferred in which the container is transported along a transport path which is curved at least in one section in which the external application device for sterilising at least one section of an outer wall of containers is disposed.

Moreover a variant of the method for sterilising containers is preferred in which a further external application device is disposed on the side of the transport path opposite the first external application device, wherein the first external application device and the further external application device are particularly preferably disposed offset along the transport path. The two external application devices are preferably offset with respect to one another by an angle between 2 and 20°, particularly preferably between 5 and 10°, of a circle of curvature of the transport path.

BRIEF DESCRIPTION OF THE DRAWINGS

Further advantages and embodiments are apparent from the appended drawings.

In the drawings:

FIG. 5 shows a representation of a lifting/rotating mechanism for moving the plastic parisons;

FIG. 6 shows a detail of the mechanism illustrated in FIG. 4;

DETAILED DESCRIPTION OF THE INVENTION

Figure 1:
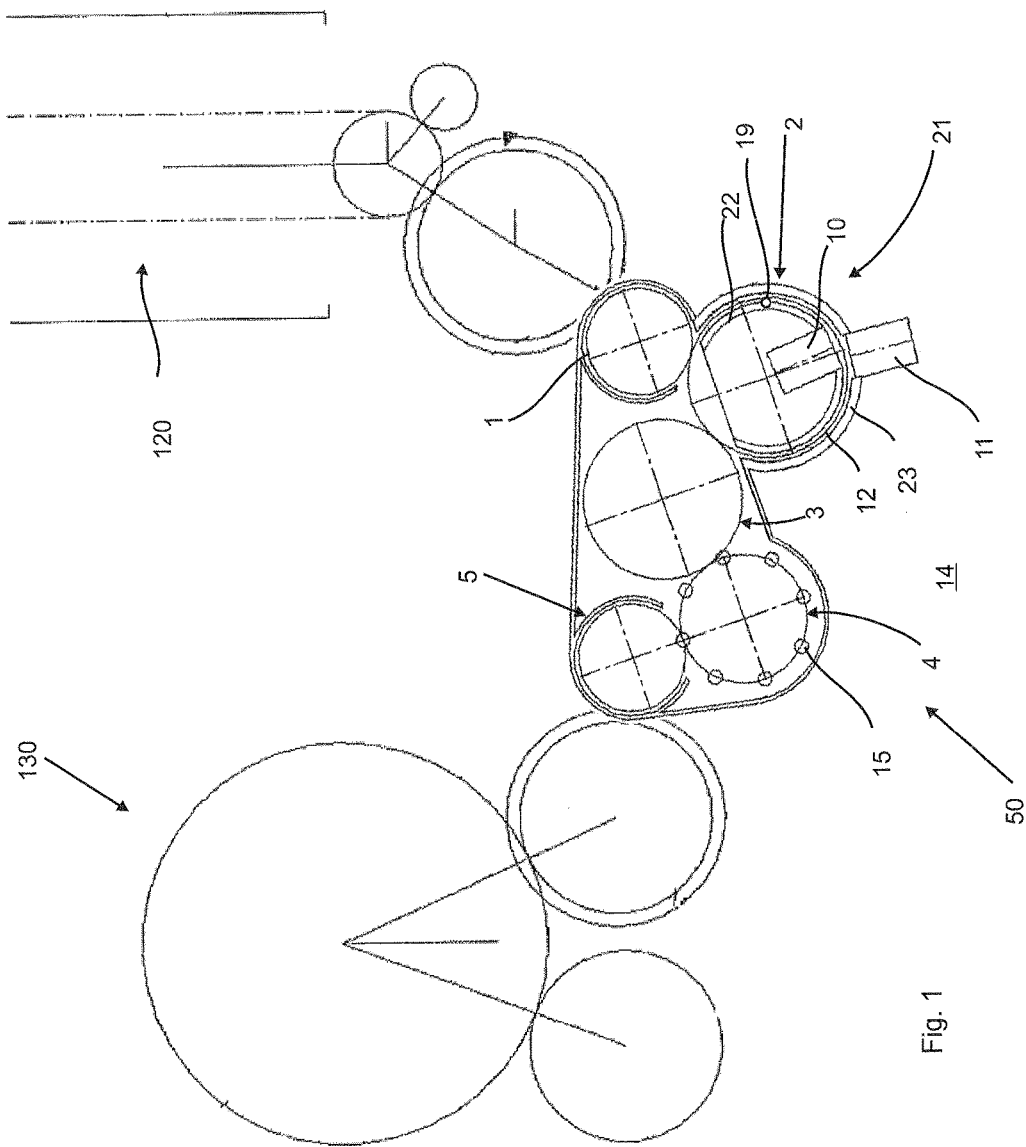
FIG. 1 shows a schematic representation of a top view of a device for sterilising containers.

FIG. 1 shows a schematic representation of a top view of a device 50 for sterilising containers 19. This has a transport device 1 for receiving containers 19 which in the illustrated embodiment is designed as a feed starwheel 1. A treatment zone for the containers 19 in which the external sterilisation takes place is located downstream with respect to the feed starwheel 1. In order to be able to apply charge carriers to the containers 19, the containers are transferred to a transport device 2 which transports the containers past the external application devices 10 and 11. During transport charge carriers are applied to the containers 19 are acted upon by charge carriers which are emitted by the external application devices 10 and 11. To enable sterilisation over the entire periphery, two external application devices 10 and 11 are provided, wherein the first external application device 10 is disposed on the radially inner side of the transport path and a second external application device 11 is disposed on the radially outer side of the transport path. However, it would also be conceivable to omit one of the two external application devices and instead to achieve a complete sterilisation of the container by a (e.g. complete) rotation of the container.

In order to shield the environment 14 against the radiation emitted by the external application devices 10 and 11, in particular by the outwardly radiating external application device 10, this region is surrounded by a strong radiation shielding system 21. For this purpose the radiation shielding system is composed of a plurality of radiation shielding devices 22 and 23 which shield the transport channel in different directions. In the illustrated top view an outer radiation shielding device 23 and an inner radiation shielding device 22 can be seen. Shielding in the downward and upward direction is not shown.

Due to the curvature of the transport path and thus also of the radiation shielding system 21 in the region of the external application devices 10 and 11 it is possible, for radiation to be reflected between the outer radiation shielding device 23 and the inner radiation shielding device 22 and so the region in which the sterilisation takes place is larger than merely the region immediately before the external application devices 10 and 11 or the charge carrier exit window.

In order to allow the containers to remain for as long as possible in the region in which the sterilisation of their outer surface takes place, a low transport speed and short distance between the containers is advantageous. Due to the short distance between two adjacent containers along the transport path, a high throughput can be achieved even at low transport speed. Furthermore, with a small pitch spacing it is advantageous that few charge carriers (or also little radiation) can pass unused for the sterilisation process between the containers.

However, in order to restore a larger pitch spacing, i.e. a greater distance between two containers directly following one another along the transport path, as is required for devices needed downstream, a distance changing device 3 is disposed downstream directly after the external sterilisation device to change the distance between two containers following one another along the transport path. By means of this distance changing device 3, in this case a pitch reduction starwheel, it is possible to vary the spacing of the containers so that a transfer to an internal sterilisation device 15 disposed downstream is possible.

The internal sterilisation device has a plurality of internal application devices 15 which can be at least partially introduced into the containers. These are disposed along or around a transport device 4 which transports the containers along the transport path during the treatment of a internal surface of the containers. For internal sterilisation each the internal application devices 15 has a so-called beam finger which is dimensioned so that it fits through an opening in the container. However, the remaining part of each internal application device 15 is usually significantly larger than the beam finger and in particular has a larger diameter. The diameter is usually also greater than that of each individual container to be sterilised, so that the distance between two containers directly following one another along the transport path in the region of the internal sterilisation device is no longer predetermined by the diameter the containers, but by a minimum spacing between two neighbouring internal application devices 15. In particular in the internal sterilisation if parisons it is therefore necessary to increase the distance between two containers directly following one another along the transport path and to adapt it to the spacing between two adjacent internal application devices 15.

From the internal sterilisation device, after treatment with an internal sterilisation device 15 the containers are delivered to a downstream transport device 5. This transport device 5, like the transport device 1, is designed as a transport starwheel 5. However, the transport starwheels 1 and 5 differ in their construction. At least the pitch spacing with which they transport containers differs. The transport starwheel 5 takes the containers which have been sterilised on an inner surface from a transport device 4 which transports the containers during the internal sterilisation and delivers them to a further transport device (not shown) or to a container treatment device. For example, a container treatment device disposed downstream of the transport starwheel 5 could be a transforming device or a filling device. The individual internal application devices 15 advantageously apply charge carriers to the entire inner surface of the containers 19.

Figure 2:
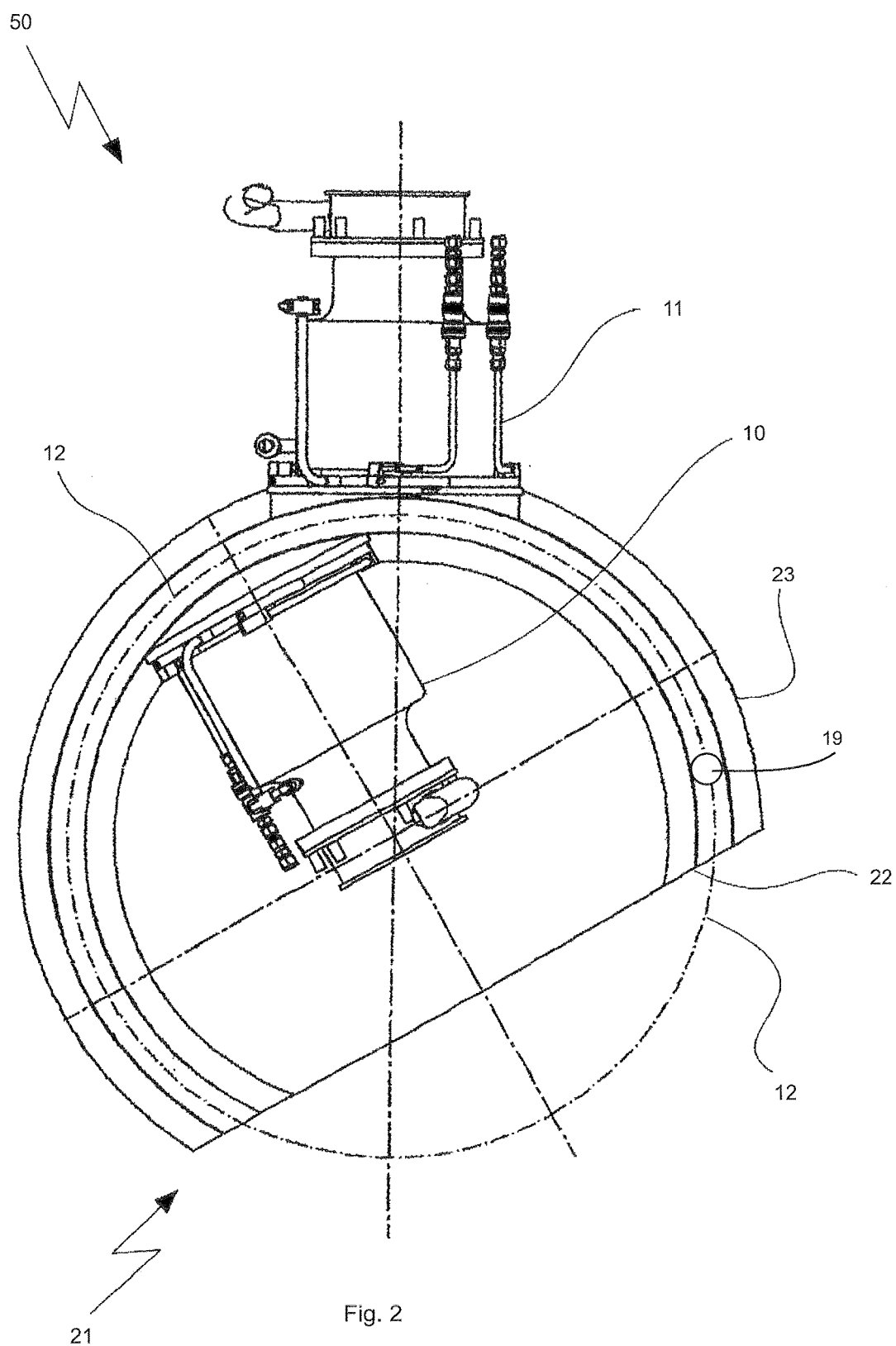
FIG. 2 shows a schematic representation of a top view of a region of a device for sterilising containers in which the external sterilisation of the containers takes place.

FIG. 2 shows a schematic representation of a top view of a region of a device for sterilising containers in which the external sterilisation of the containers takes place.

In particular FIG. 2 shows a section of the transport path along which the external sterilisation of the containers 19 takes place. For external sterilisation the containers are guided past the external application devices 10 and 11. These external application devices 10 and 11 are disposed on different sides of the transport path and thus are suitable for applying charge carriers to a container 19 from different sides. As a result the transport mechanism for the containers 19 can be simplified, since a complete rotation of the containers 19 is not necessary for application of charge carriers over the entire periphery. The external application devices 10 and 11 advantageously apply charge carriers to the entire external circumferential surface of the containers 19.

The two external application devices 10 and 11 are not directly opposite one another, but are disposed offset relative to one another along the transport path of the containers 19. During transport of the containers along the transport path which runs clockwise (to the right) in the view shown in FIG. 2, the containers first reach the sphere of influence of the external application device 10 lying radially on the inside and accelerating charge carriers radially towards the outside. There an external surface lying radially on the inside in relation to the transport device 2 of the container is exposed to charge carriers.

Only somewhat further downstream the containers 19 enter the sphere of influence of the external application device 11 lying radially on the outside and accelerating charge carriers radially towards the inside. The outer surface of the container, lying radially on the outside in relation to the transport device (2) and lying in the charge carrier shadow of the container during treatment by the other external application device 10, has charge carriers applied to it in this region to charge carriers by the external application device 11.

The two external application devices 10 and 11 are offset with respect to one another by a predetermined angle with respect to the centre or the axis of rotation of the transport device 2. This offset can ensure that the charge carriers of the two external application devices 10 and 11 are not accelerated directly onto each other, whereby in long-term operation damage could be caused to the external application devices 10 and 11. Also the containers 19 can become heated when exposed to charge carriers as they at least partly absorb the kinetic energy of the accelerated charge carriers and convert it into thermal energy. Thus due to the offset arrangement of the external application devices 10 and 11 overheating and hence possible damage to the containers can be avoided with simultaneous application of charge carriers from two external application devices 10 and 11.

Furthermore the length of the section of the transport path in which the containers are exposed to charge carriers is extended. With a cloud-like propagation of charge carriers in which the charge carriers are also subjected to diffusion in addition to the preferred direction predetermined by the charge carrier acceleration device, an overlap of the emitted charge carrier clouds is therefore also possible so that the containers 19 stay longer in the common charge carrier cloud of both external application devices 10 and 11.

In order to shield the environment 14 from the emitted charge carriers and/or from the radiation emitted during charge carrier generation, the region of the external sterilisation is surrounded by a strong radiation shielding system 21. This consists at least of the radiation shielding devices 22 and 23 which surround the transport path on different sides. With regard to the centre of the transport device 2 (in particular the axis of rotation of the transport device 2), one radiation shielding device 23 is disposed radially outside the transport channel and one radiation shielding device 22 is disposed radially inside the transport channel. The shielding of the transport channel perpendicular to the drawing plane is not shown.

The radiation shielding system 21 in the region of the external application devices 10 and 11 follows the curvature of the transport path and thus enables radiation to be reflected between the outer radiation shielding device 23 and the inner radiation shielding device 22. In this way the region in which the containers are exposed to charge carriers and/or energy-rich (sterilising) radiation can be enlarged.

Figure 3:
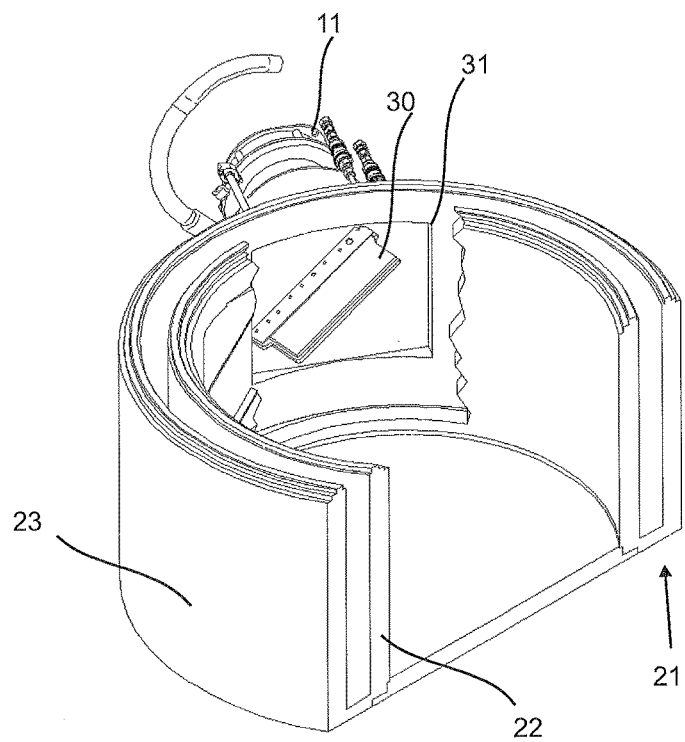
FIG. 3 shows a perspective view of a plant according to the invention for sterilising containers.

FIG. 3 shows a schematic representation of an oblique view of a region of a device for sterilising containers in which the external sterilisation of the containers 19 takes place, with the additional representation of a charge carrier exit window 30.

As in FIG. 2, the transport channel surrounded by the radiation shielding system 21, and an external application device 11 are shown. The external application device 10 lying radially inside in relation to the centre of the transport device 2 (not shown) and the part of the inner radiation shielding device 22 lying in this region are not shown in order to be able to represent the arrangement of the external application device 11 and its charge carrier exit window 30.

As can be seen in FIG. 3, the external radiation shielding device 23 is interrupted in the region of the external application device 11 in order to enable entry into the transport channel for the charge carriers generated in the external application device 11. For this purpose a housing of the external application device 11 terminates the transport channel in a flush manner in order to prevent contamination of the transport channel designed as a clean room. The flush connection of the external application device 11 is achieved by a fastening element 31, in this case a fastening flange. In order to allow unhindered passage of the charge carriers into the clean room or transport channel the external application device 11 has a charge carrier exit window 30 through which charge carriers can be accelerated by a charge carrier generation device in the direction of the transport channel. Thus, it is possible for the charge carriers to reach the interior of the clean room through the charge carrier exit window 30 and there to meet a container 19 transported along the transport path.

The charge carrier exit window 30 has a substantially rectangular cross-section. Although other geometries of the charge carrier exit window 30 are also possible, such as circles, ovals and/or a square as a special form of a rectangle, a rectangular form or a parallelogram form with unequal side lengths is preferred. In the rectangular form shown, the main axes are oriented so that they are inclined with respect to the transport path (or the horizontal vector part thereof). Thus it is possible for a container 19 guided past a charge carrier exit window 30 to remain longer in the sphere of influence of the charge carrier cloud. Thus with comparable sterilisation power a more compact construction can be achieved.

In particular if the container 19 can be raised by a lifting mechanism during transport along the circular path of the transport channel and thus can follow the course of the charge carrier exit window 30, an extension of the treatment region is possible.

Figure 4:
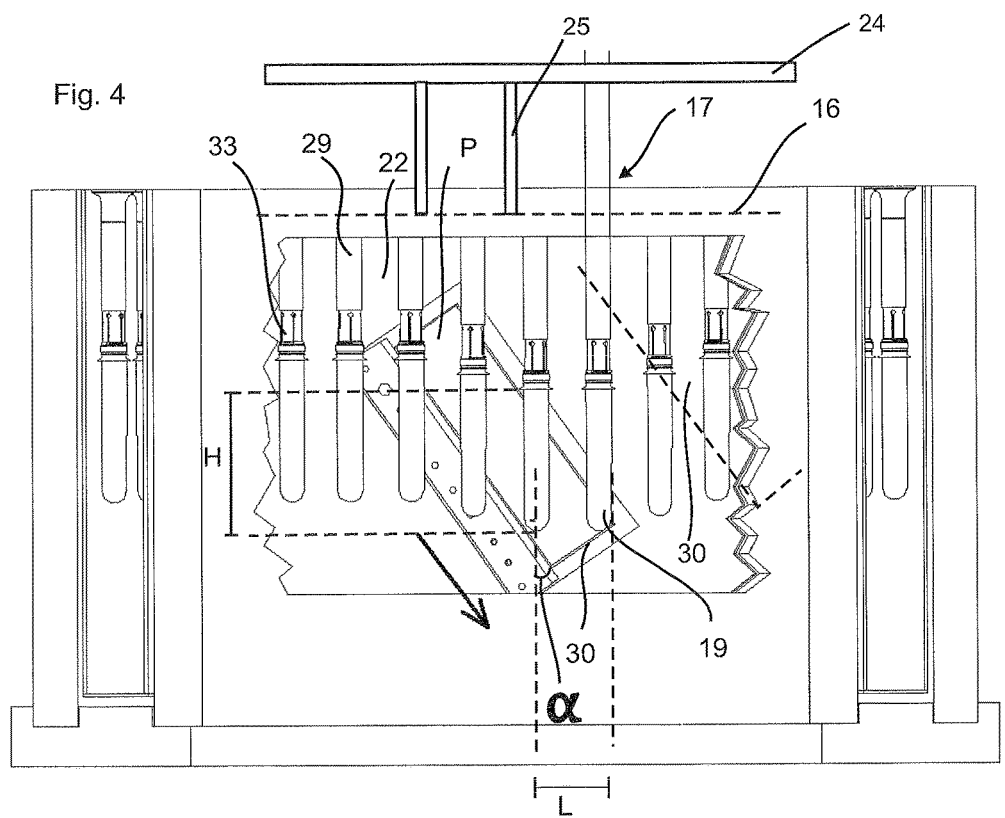
FIG. 4 shows a side view of a device for sterilising containers.

This can be seen in particular in the schematic representation of a side view shown in FIG. 4. FIG. 4 shows a side view of a region of a device 50 for sterilising containers 19 in which the external sterilisation of containers takes place, with the additional representation of the charge carrier exit window 30. In order to show clearly that the charge carrier exit windows 30 of several external application devices 10 and 11 can be disposed so that they are inclined by an angle α with respect to the transport path (or the horizontal vector part thereof) and/or the longitudinal axis of the container, several charge carrier exit windows 30 are shown. These can also be disposed so that they are inclined with respect to one another. Thus, it is possible that the containers 19 which are raised in the region of an external application device 10 along the transport path (or moved in the direction along the container longitudinal axis) can be lowered again in the region of the next external application device 11 along the transport path (or moved in the opposite direction relative to the first movement along the container longitudinal axis).

Due to the orientation of the charge carrier exit window 30 which is inclined by an angle α with respect to the longitudinal axis of the container, the section along which direct external sterilisation can take place during transport of the container 19 is extended. Even during an exclusive movement of the container 19 perpendicular to its longitudinal axis, the section of the transport path along which a section of the outer wall of the containers 19 is exposed to charge carrier radiation is extended. If we consider for example the side sheathing of the base of a container 19, this is located in the direct influence of the charge carriers emitted vertically by the external application device 11 onto the container along a section of the transport path (length L of the parallelogram P shown). This length L (according to the trigonometric functions or angular function) is extended in relation to the width of the exit window by a factor which corresponds to the reciprocal value of the sine of the angle of inclination (i.e. the cosecant of the angle of inclination).

In this case the inclination of the charge carrier exit window 30 is selected so that the overlap region of the charge carrier exit window 30 with the area covered during transport of the container 19 by its vertical projection onto the charge carrier exit window 30 has at least a height H which corresponds to the length of the container in its longitudinal direction. In the example shown the overlap region has the shape of a parallelogram of length L and height H (over L). However, depending upon the shape of the charge carrier exit window 30, the orientation of the container 19 in relation to the transport path and the course of the transport path, other geometries of the overlap region are also possible.

In order to allow a particularly compact design of the device, as shown in FIG. 4 it is proposed that the container 19, during its transport along the transport path, can also be moved along the longitudinal axis of the container (at least with one vector component). If the container 19 shown in FIG. 4 is moved during its sterilisation not only horizontally (or parallel to the length L) but also in the height direction H, it is possible to keep the container even longer in the sphere of influence of the charge carriers.

For this purpose the transport device 2 has a lifting device 17 (only shown schematically). This lifting device 17 is connected to a substantially horizontal support plate 24 which is connected to the transport device and follows its horizontal movement, in this case the rotational movement of the transport device 2. The lifting device 17 is disposed outside the clean room. Thus maintenance work is simplified. A holding element 33 which carries the container during its transport along the transport path is located in the interior of the clean room and is connected to the lifting device 17. The connection between the holding element 33 and the lifting device 17 is achieved by a carrier 29 which penetrates an upper radiation shielding device 24. The upper radiation shielding device 24 is mounted movably relative to the radiation shielding devices 22 and 23 and moves parallel to the support plate 24. Therefore the radiation shielding device 24 has openings through which the carrier 29 can be guided. To be able to maintain the screening properties of the radiation shielding device 24 even during movement of the carrier 29 or the container in its longitudinal direction, the carrier 29 comprises at least in sections a shielding material by which the openings in the radiation shielding device 24 can be sealed both in relation to charge carriers and radiation, and in relation to contamination of the clean room.

In order to guarantee that the lifting devices 17 connected to the support plate 24 and the openings in the radiation shielding device 16 move synchronously with one another in such a way that a lifting device 17 is disposed above an opening in the radiation shielding device 16, the support plate 24 and the radiation shielding device 16 are connected to one another via support elements 25.

In FIG. 1 the reference 120 relates to a heating device for heating plastic parisons and the reference 130 relates to a transforming device for transforming plastic parisons into plastic containers. It will be recognised that here the two external sterilisation devices 11 are each inclined or their exit windows are each inclined, as has already been illustrated in FIG. 4. These two inclined positions are also opposed and preferably axially symmetrical with an axis of symmetry extending between these two exit windows. In this way, if for example we assume a movement of the plastic parisons in a clockwise direction, first of all the plastic parisons are guided past the right external sterilisation device and simultaneously lowered.

Subsequently the plastic parisons can be raised again when they pass the left external sterilisation device. At the same time the plastic parisons, as mentioned above, can also be rotated by the driving devices 104. In this way will a very quick sterilisation is achieved. As mentioned above, reflector elements for the electrons can be disposed on the corresponding inner wall 22 in order also in this way to improve the irradiation of the plastic parisons.

FIG. 5 shows a representation for illustration of the combined lifting/rotating mechanism for the individual plastic parisons 19. These are in each case disposed on a carrier 29 and holding devices 29a. These retaining devices 29a engage here in the mouths of the plastic parisons and are preferably biased against this inner wall of the mouths of the plastic parisons 19.

The reference numeral 84 identifies a gaiter which serves for sealing a lifting movement. A further support element 85 extends through a clean room boundary. The reference numeral 82 here designates a compression spring which serves for in order to lift the plastic parisons 19. The reference 104 designates a driving device, such as a drive motor, which effects a rotary movement of the plastic parisons. The reference numeral 102 identifies a curve roller which can roll with respect to a guide curve (not shown) in order thus to carry out the lifting movement. The reference sign 92 designates a bearing block which serves for holding the device for carrying out the lifting movement. Accordingly the lifting movement is enabled by means of an axial bearing 94. A bearing bush 87 is provided at the end of the gaiter 84. This bush serves here precisely as a gripping bush and is axially movable. The reference 93 identifies a rotary seal. Due to the arrangement, if required the rotary movement and the lifting movement can also be carried out simultaneously.

The reference 18 identifies in its entirety an axial and radial bearing for mounting the rotary shaft 85. The reference numeral 99 identifies an intermediate part for X-ray shielding. A rotary bearing 27 is provided to support the rotary movement.

FIG. 6 shows an enlarged view of a detail of the arrangement shown in FIG. 5 for better representation.

Figure 7:
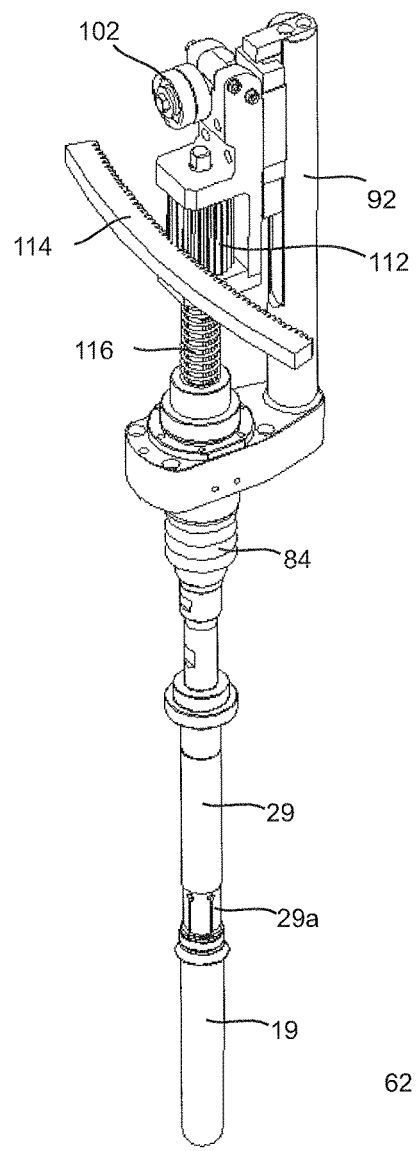
FIG. 7 shows a further representation of the rotating mechanism.

FIG. 7 shows a further possible embodiment of a possible rotary drive. This rotary drive has a curve roller 102 provided for carrying out the lifting movement, but here the rotary movement takes place via tooth systems which are displaceable against one another. More precisely here a first gear 112 is provided which is designed here as a long wheel. Furthermore a hollow gear 114 is provided which engages with the gear 112 and in this way enables the rotary movement. The reference 116 designates a spring device, which serves to pretension the lifting movement and pulls the parison 19 upwards. Instead of a hollow gear a hollow toothed belt can be provided, which here too can have an internal tooth system. Such a (hollow) toothed belt is advantageously of flexible construction. In addition a driving device such as a motor (not shown) can be provided, which drives this hollow gear or a corresponding hollow toothed belt.

In this way it is possible to influence the rotation of the parisons or containers so that the dose distribution occurs uniformly. In this way on the one hand a means of influencing the rotation of the containers is retained and on the other hand it is not necessary to provide a discrete servomotor on each rotary unit.

Figure 8:
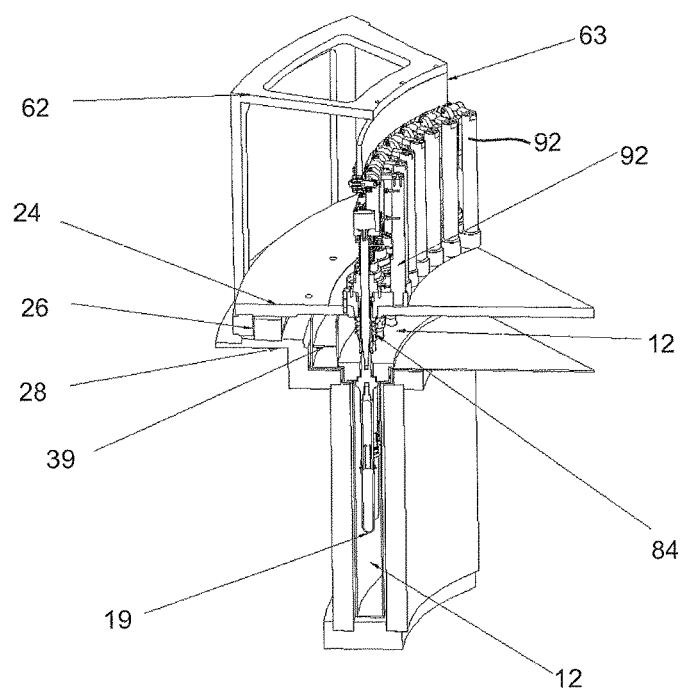
FIG. 8 shows a further detail view of the device according to the invention.

FIG. 8 shows a further possible representation of the device according to the invention. Here too the lifting curve 63 is shown, which is disposed on a holder 62. The reference 12 designates a clean room, through which the plastic parisons are passed. The reference 14 designates the surroundings of this clean room (which is unsterile).

The reference 39 identifies an air channel and the reference 28 a support plate which serves for supporting the arrangement. The reference 24 identifies a further support plate for the lifting unit, and the reference 26 identifies a ball turning connector.

Generally the plastic parisons are transported on a star wheel past an emitter thereby disinfected. This results in a changing distance between the plastic parison and the generally planar exit window of the radiation device. In order to compensate for dose differences in doses in the treatment, caused by the different distances, it would be conceivable to carry out the rotation as a function of this distance of the plastic parison from the emitter. In this way it would also be possible to configure the dose distribution very homogeneously and uniformly, even though the distance from the radiation device changes.

Figure 9:
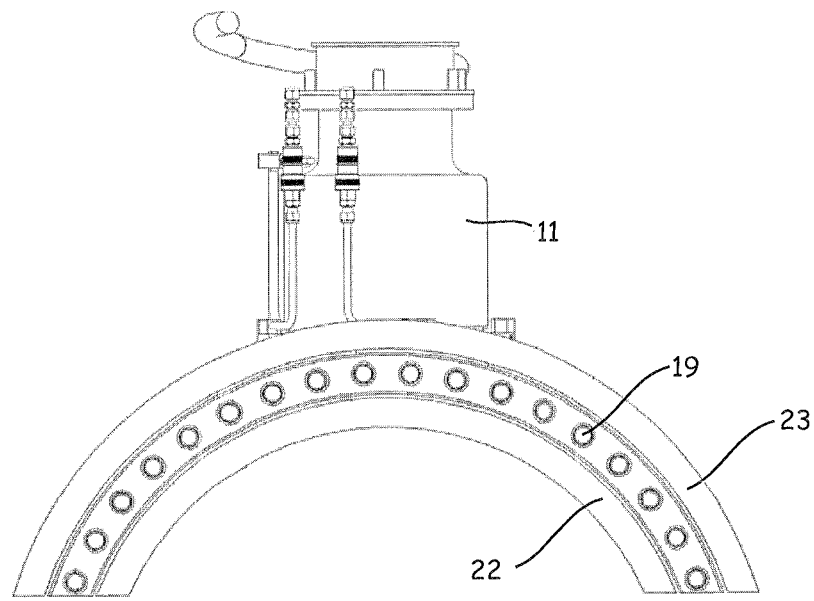
FIG. 9 shows a further plan view of a device according to the invention.
Figure 10:
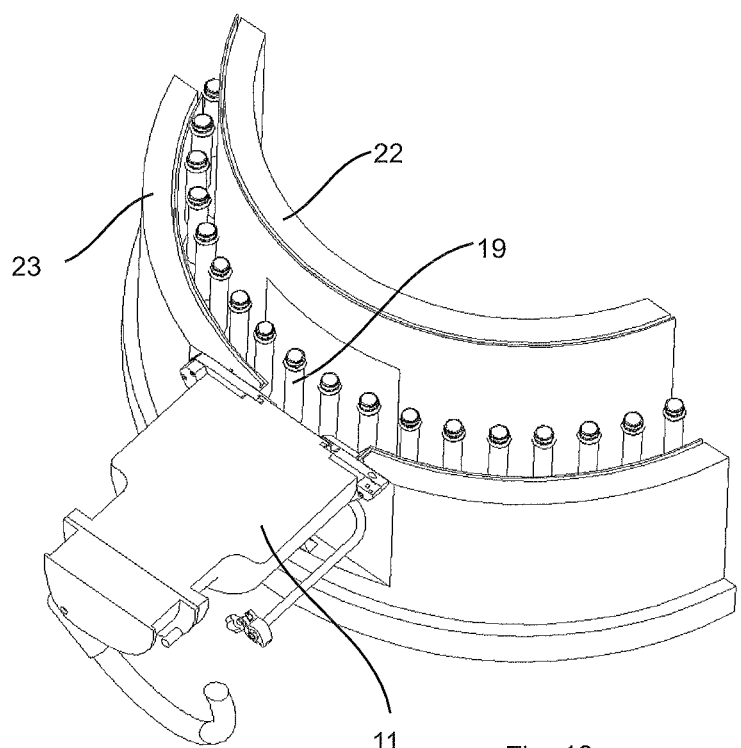
FIG. 10 shows an oblique view of the representation in FIG. 7.

FIGS. 9 and 10 show two further simplified representations of a device according to the invention, wherein here too the transport path of the parisons 19 through the space formed between the radially inner radiation shielding device and the radially outer radiation shielding device is illustrated. Also the external application device 11 is again shown.

Figure 11:
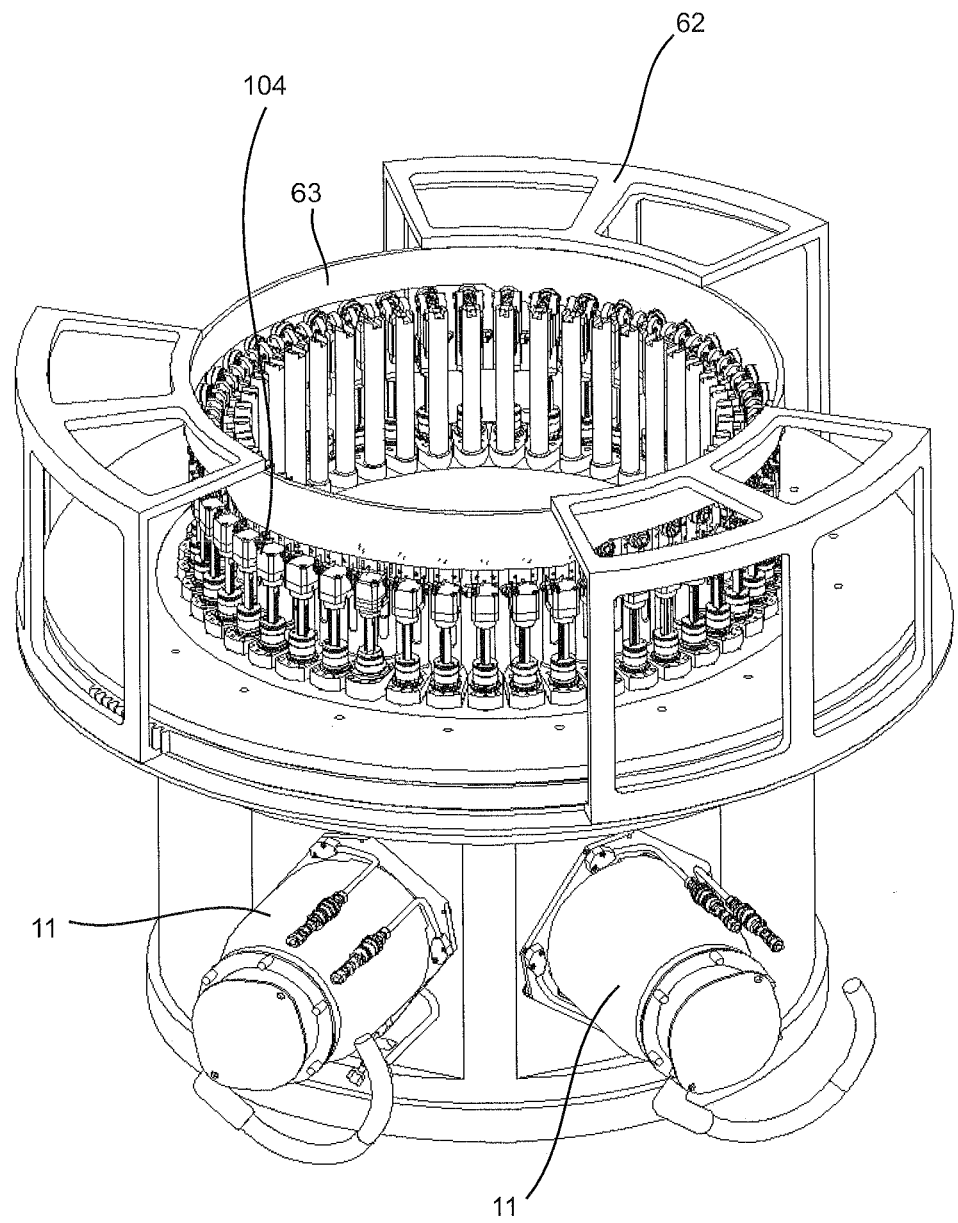
FIG. 11 shows an overall representation of a device according to the invention.

FIG. 11 shows an overall representation of the device according to the invention Here too the individual drives 104 for producing the rotary movement can again be seen, as well as the guide curve 63 which is responsible for the lifting movement. For this embodiment two external sterilisation devices are provided which are disposed radially outside the transport path of the plastic parisons.

In this case the external sterilisation devices can, as mentioned above, have exit windows through which the charge carriers or electrons can exit. These exit windows have at least in sections a film, in particular formed of titanium. This titanium film advantageously has a thickness between 2 μm and 30 μm, preferably between 5 μm and 20 μm and particularly preferably between 6 μm and 14 μm. Furthermore a cooling unit is advantageously provided for cooling this exit window. In this case application devices are provided which supply the exit window with a liquid and/or gaseous medium. In addition cooling grids can also be provided, on which the exit windows rest. These cooling grids can have a cooling medium flowing through them.

The applicant reserves the right to claim all the features disclosed in the application documents as essential to the invention in so far as they are individually or in combination novel over the prior art.

LIST OF REFERENCES 1 feed starwheel
2 transport device
3 distance changing device
4 transport device/rotary device
5 transport device/transport starwheel
10 external application device
11 external application device
12 clean room
14 surroundings
15 internal sterilisation device
16 radiation shielding device
17 lifting device/moving device
18 axial and radial bearing
19 containers/plastic parisons
21 radiation shielding system
22 radiation shielding device
23 radiation shielding device
24 support plate
25 support element
27 rotary bearing
29 carrier
29a holding devices
30 charge carrier exit window
31 fastening element
33 holding element
39 air channel
50 device
60 coupling device
62 holder
63 guide curve
82 compression spring
84 gaiter
85 rotary shaft
87 bearing bush
92 bearing block
93 rotary seal
94 axial bearing
99 intermediate part for X-ray shielding
102 curve roller
104 driving devices/drives
112 gear
114 hollow gear
116 spring device
120 heating device
130 transforming device
H height
L length/longitudinal direction
U surrounding environment
P parallelogram
α angle

The invention claimed is:

1. A system for sterilizing plastic containers, comprising a transport device for transporting the containers during the sterilization along a predefined circular transport path, a clean room within which the containers are transported during the sterilization of the containers, wherein the clean room is delimited by at least one wall with respect to the clean room environment, a first external application device for sterilizing at least a section of an outer wall of the containers, wherein in a region of the transport path in which the first external application device for sterilizing is disposed, the first external application device for sterilizing is surrounded at least in sections by a radiation shielding system having at least one outer radiation shielding device disposed radially outside the circular transport path and one inner radiation shielding device disposed radially inside the circular transport path, by which radiation emitted by the first external application device for sterilizing can be at least partially absorbed, so that with said at least one outer and said at least one inner radiation shielding devices a transport channel is realized which extends between the at least one outer and said at least one inner radiation shielding devices and in which the containers can be transported, wherein the external application device has a source of charge carriers for generation of charge carriers, and a first moving device and a carrier for moving the containers at least intermittently in a longitudinal direction during the sterilization of the containers, a drive device driving the carrier, said drive device having a drive axis which is parallel to a longitudinal direction of the containers, a longitudinal extension of the carrier being parallel to said drive axis of the drive device and parallel to the longitudinal direction of the container, wherein the system has a rotary device for rotating the containers about the longitudinal direction of the containers at least intermittently during the sterilization, wherein the rotary device and the moving device are configured such that a rotation of the containers is enabled during a movement of the containers in the longitudinal direction of the containers, said system further comprising a mechanical coupling device for coupling together the movement of the containers in the longitudinal direction of the containers and the rotary movement of the containers about the longitudinal direction of the containers.

2. The system as claimed in claim 1, wherein at least one element of the rotary device is disposed outside the clean room.

3. The system as claimed in claim 1, wherein at least one element of the moving device is disposed outside the clean room.

4. The system as claimed in claim 1, further including at least one sealing device for sealing the movement of the containers in the longitudinal direction of the containers and/or the rotation of the containers about the longitudinal direction of the containers.

5. The system as claimed in claim 1, further including at least one reflector element for reflecting electrons, disposed so that the containers can be transported between the first external application device and the reflector element.

6. The system as claimed in claim 1, wherein the mechanical coupling device has two inter engaging gears.

7. The system as claimed in claim 6, wherein one gear is displaceable with respect to the other gear whilst retaining an engagement between the gears.

8. The system as claimed in claim 1, wherein the external application device has an exit window through which accelerated charge carriers can exit, wherein the exit window has at least in sections a thin sheet of material.

9. The system as claimed in claim 1, wherein the mechanical coupling device comprises a flexible toothed belt.

10. The system as claimed in claim 1, wherein the mechanical coupling device has at least one coupling element which is moveable in two opposing directions of movement.

11. The system as claimed in claim 1, wherein the mechanical coupling device has at least one coupling element which coupling element is driven by the driving device, which drives a further coupling element.

12. The system as claim in claim 11, wherein the drive device comprises a servomotor.

13. The system as claimed in claim 11, wherein the mechanical coupling element comprises inter engaging tooth systems.

14. The system as claimed in claim 13, wherein the inter engaging tooth systems comprise toothed belts or toothed wheels.

15. The system as claimed in claim 13, wherein at least one of the inter engaging tooth systems is driven by the drive device.

16. The system as claimed in claim 15, wherein the drive device comprises an electric motor.

17. The system as claimed in claim 1, wherein the rotary device includes a first gear which is displaceable with respect to a second gear whilst retaining an engagement between the first and second gears.

18. The system as claimed in claim 17, wherein at least one of the first and the second gears is a toothed belt.

19. The system as claimed in claim 18, wherein the toothed belt is disposed stationary and the second gear is disposed displaceably with respect thereto.

20. The system as claimed in claim 19, wherein the second wheel directly drives the rotary device for rotating the containers.

21. The system as claimed in claim 1, wherein the containers are plastic parisons.

22. A method for sterilizing plastic containers comprising providing the system of claim 1 and transporting the containers with the transport device within the clean room and during said transport external surfaces of the containers are sterilized by irradiation with charge carriers, wherein the containers are moved at least intermittently in the longitudinal direction of the containers, and are rotated about the longitudinal direction of the containers at least intermittently, during the sterilization of the containers.

23. A method as claimed in claim 22, wherein movement of the containers in the longitudinal direction of the containers and/or the rotation of the containers about the longitudinal direction of the containers is sealed.

* * * * *